(12) United States Patent
Browder et al.

(10) Patent No.: US 12,307,065 B1
(45) Date of Patent: May 20, 2025

(54) SYSTEM REPRESENTATION OF AN EXECUTION SEQUENCE WITHIN A GRAPHICAL USER INTERFACE

(71) Applicant: Signet Health Corporation, North Richland Hills, TX (US)

(72) Inventors: Blake Browder, Dallas, TX (US); Joy Figarsky, Little Rock, AR (US)

(73) Assignee: Signet Health Corporation, North Richland Hills, TX (US)

( * ) Notice: Subject to any disclaimer, the term of this patent is extended or adjusted under 35 U.S.C. 154(b) by 0 days.

(21) Appl. No.: 18/957,784

(22) Filed: Nov. 24, 2024

(51) Int. Cl.
*G16H 10/60* (2018.01)
*G06F 3/0481* (2022.01)
*G06F 3/0486* (2013.01)

(52) U.S. Cl.
CPC .......... *G06F 3/0481* (2013.01); *G16H 10/60* (2018.01); *G06F 3/0486* (2013.01)

(58) Field of Classification Search
CPC ..................................................... G16H 10/60
USPC ........................................................ 715/772
See application file for complete search history.

(56) References Cited

U.S. PATENT DOCUMENTS

| | | | | |
|---|---|---|---|---|
| 10,902,341 | B1* | 1/2021 | Qureshi | G06Q 10/10 |
| 11,976,265 | B2* | 5/2024 | Gonzalez | C12N 1/00 |
| 12,080,286 | B2* | 9/2024 | Nouri | G10L 25/63 |
| 2003/0050801 | A1* | 3/2003 | Ries | G16H 10/60 |
| | | | | 705/2 |
| 2004/0111293 | A1* | 6/2004 | Firanek | G16H 40/20 |
| | | | | 705/2 |
| 2007/0168225 | A1* | 7/2007 | Haider | G16H 10/20 |
| | | | | 128/920 |
| 2007/0226005 | A1* | 9/2007 | Smith | G16H 70/20 |
| | | | | 707/999.001 |
| 2010/0124731 | A1* | 5/2010 | Groscurth | A61B 6/506 |
| | | | | 700/98 |
| 2012/0323827 | A1* | 12/2012 | Lakshmanan | G06F 17/18 |
| | | | | 706/12 |
| 2015/0058043 | A1* | 2/2015 | Heinemann | G16H 10/60 |
| | | | | 705/3 |
| 2016/0210424 | A1* | 7/2016 | Di Battista | G16H 10/60 |
| 2017/0286626 | A1* | 10/2017 | Jayakumar | G16H 15/00 |
| 2018/0158539 | A1* | 6/2018 | Gupta | G16H 10/60 |
| 2018/0277244 | A1* | 9/2018 | Gupta | G06F 3/04842 |
| 2018/0342313 | A1* | 11/2018 | Gupta | G16H 50/20 |

(Continued)

*Primary Examiner* — Reza Nabi
(74) *Attorney, Agent, or Firm* — Caldwell Intellectual Property Law

(57) ABSTRACT

A system for generating a visual representation of an execution sequence within a graphical user interface, including: at least a computing device, wherein the computing device comprises: a memory; a display device; and at least a processor configured to generate a display data structure including: providing a plurality of visual elements associated with execution sequence data and action sequence data and at least an event handler; linking a first visual element to the execution sequence data, linking a second visual element to the action sequence data; verifying the action sequence data; adjust the execution sequence data as a function of the verified action sequence data; classify the adjusted execution sequence data to a status; linking a third visual element to the status; generate the display data structure; and configure, using the display data structure, the display device to display the data structure.

18 Claims, 9 Drawing Sheets

(56) References Cited

U.S. PATENT DOCUMENTS

| | | | |
|---|---|---|---|
| 2020/0164231 A1* | 5/2020 | Cannata | A61N 7/00 |
| 2021/0142000 A1* | 5/2021 | Vis | G06F 3/0481 |
| 2021/0158941 A1* | 5/2021 | Taylor | G16H 15/00 |
| 2021/0165829 A1* | 6/2021 | Dornbush | G06Q 10/103 |
| 2021/0201240 A1* | 7/2021 | Yanamala | G06Q 10/063114 |
| 2021/0303578 A1* | 9/2021 | Dua | G06F 16/243 |
| 2021/0303636 A1* | 9/2021 | Dua | G06F 16/9038 |
| 2022/0398547 A1* | 12/2022 | Wang | G06N 20/00 |
| 2022/0406427 A1* | 12/2022 | Bayuzick | G16H 10/60 |
| 2023/0244989 A1* | 8/2023 | Riva | G06N 3/045 |
| | | | 706/11 |
| 2023/0351351 A1* | 11/2023 | Nguyen | G06Q 30/0641 |
| 2024/0008957 A1* | 1/2024 | Mednikov | G16H 30/40 |

* cited by examiner

SYSTEM REPRESENTATION OF AN EXECUTION SEQUENCE WITHIN A GRAPHICAL USER INTERFACE

FIELD OF THE INVENTION

The present invention generally relates to the field of user interfaces. In particular, the present invention is directed to a system for generating a visual representation of an execution sequence within a graphical user interface.

BACKGROUND

Present graphical user interfaces (GUIs) frequently lack the capability to reflect ongoing data updates seamlessly and often require significant processing power to manage iterative changes. Additionally, many existing systems struggle to provide accurate real-time comparisons without depending heavily on simulated or pre-generated data, which can impact dependability.

SUMMARY OF THE DISCLOSURE

In an aspect, a system for generating a visual representation of an execution sequence within a graphical user interface, wherein the system includes: at least a computing device, wherein the computing device comprises: a memory; a display device, wherein the display device displays a graphical user interface (GUI); and at least a processor communicatively connected to the memory, wherein the memory contains instructions configuring the at least a processor to: generate a display data structure, wherein generating the display data structure further includes: providing a plurality of visual elements associated with execution sequence data and action sequence data and at least an event handler; linking a first visual element to the execution sequence data, wherein the execution sequence data includes specific execution sequence data; linking a second visual element to the action sequence data; verifying the action sequence data using a verification module; adjust the execution sequence data as a function of the verified action sequence data; classify the adjusted execution sequence data to a status using a classifier; linking a third visual element to the status; generate the display data structure using the plurality of visual elements and the at least an event handler; and configure, using the display data structure, the display device to display the data structure.

In another aspect a method for generating a visual representation of an execution sequence within a graphical user interface, wherein the method includes: generating, by at least a processor, a display data structure, wherein generating the display data structure further includes: providing a plurality of visual elements associated with execution sequence data and action sequence data and at least an event handler; linking a first visual element to the execution sequence data, wherein the execution sequence data comprises specific execution sequence data; linking a second visual element to the action sequence data; verifying the action sequence data using a verification module; adjust the execution sequence data as a function of the verified action sequence data; classify the adjusted execution sequence data to a status using a classifier; linking a third visual element to the status; generating, by the at least a processor, the display data structure using the plurality of visual elements and the at least an event handler; and configuring, using the display data structure, the display device to display the data structure.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

At a high level, aspects of the present disclosure are directed to systems and methods for generating a visual representation of an execution sequence within a graphical user interface. In an embodiment, a system for generating a visual representation of an execution sequence within a graphical user interface, wherein the system includes: at least a computing device, wherein the computing device comprises: a memory; a display device, wherein the display device displays a graphical user interface (GUI); and at least a processor communicatively connected to the memory, wherein the memory contains instructions configuring the at least a processor to: generate a display data structure, wherein generating the display data structure further includes: providing a plurality of visual elements associated with execution sequence data and action sequence data and at least an event handler; linking a first visual element to the execution sequence data, wherein the execution sequence data includes specific execution sequence data; linking a second visual element to the action sequence data; verifying the action sequence data using a verification module; adjust the execution sequence data as a function of the verified action sequence data; classify the adjusted execution sequence data to a status using a classifier; linking a third visual element to the status; generate the display data structure using the plurality of visual elements and the at least an event handler; and configure, using the display data structure, the display device to display the data structure.

Figure 1:
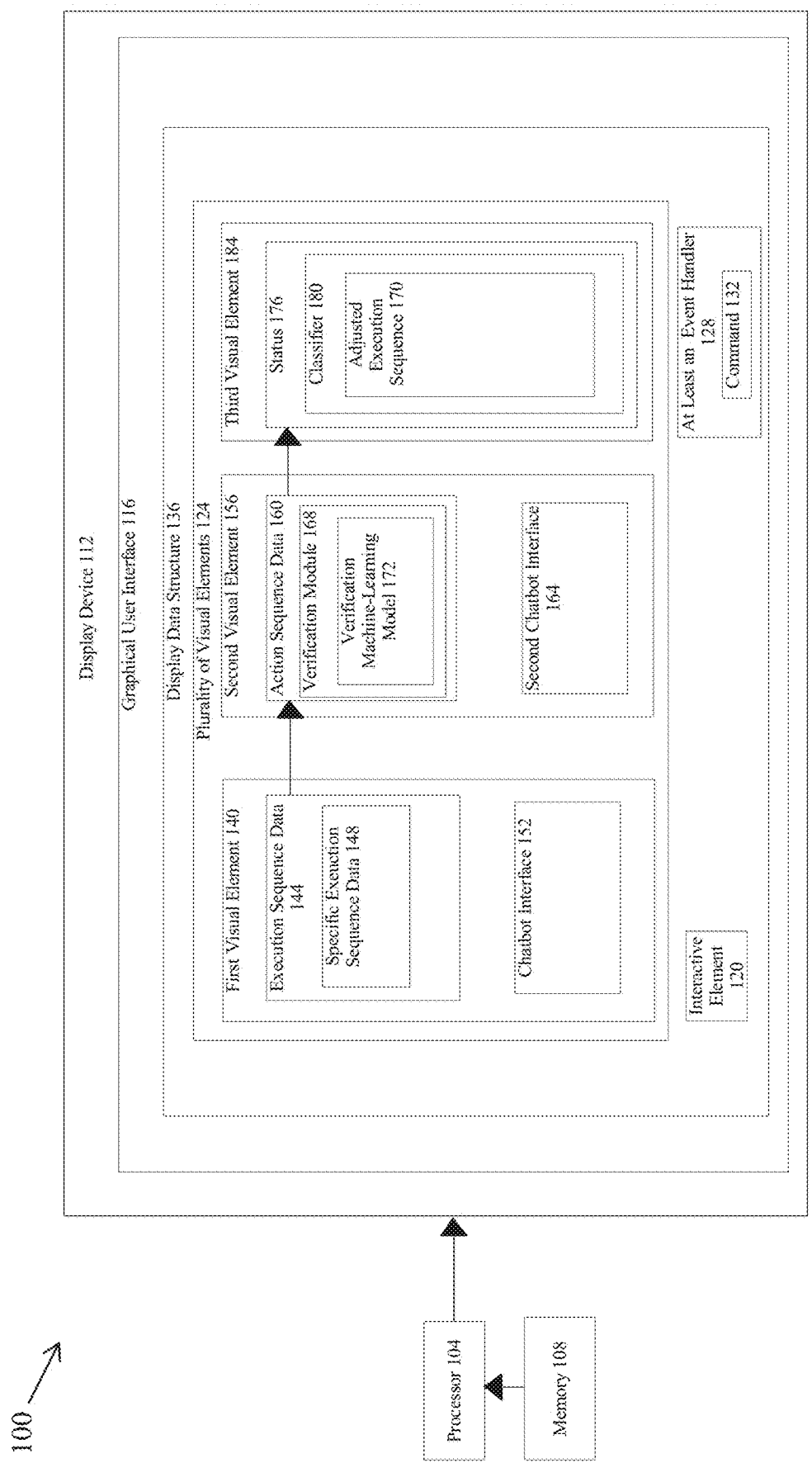
FIG. 1 is a flow diagram illustrating a system for generating a visual representation of an execution sequence within a graphical user interface.

Referring now to FIG. 1, an exemplary embodiment of a system for generating a visual representation of an execution sequence within a graphical user interface is illustrated. System 100 may include a processor 104 communicatively connected to a memory 108. As used in this disclosure, "communicatively connected" means connected by way of a connection, attachment, or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 108 may include a primary memory and a secondary memory. "Primary memory" also known as "random access memory" (RAM) for the purposes of this disclosure is a short-term storage device in which information is processed. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor 104. In one or more embodiments, data is transferred from secondary to primary memory wherein processor 104 may access the information from primary memory.

Still referring to FIG. 1, system 100 may include a database. The database may include a remote database. The database may be implemented, without limitation, as a relational database, a key-value retrieval database such as a NOSQL database, or any other format or structure for use as database that a person skilled in the art would recognize as suitable upon review of the entirety of this disclosure. The database may alternatively or additionally be implemented using a distributed data storage protocol and/or data structure, such as a distributed hash table or the like. The database may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, system 100 may include and/or be communicatively connected to a server, such as but not limited to, a remote server, a cloud server, a network server and the like. In one or more embodiments, the computing device may be configured to transmit one or more processes to be executed by server. In one or more embodiments, server may contain additional and/or increased processor power wherein one or more processes as described below may be performed by server. For example, and without limitation, one or more processes associated with machine learning may be performed by network server, wherein data is transmitted to server, processed and transmitted back to computing device. In one or more embodiments, server may be configured to perform one or more processes as described below to allow for increased computational power and/or decreased power usage by the system computing device. In one or more embodiments, computing device may transmit processes to server wherein computing device may conserve power or energy.

Further referring to FIG. 1, system 100 may include any "computing device" as described in this disclosure, including without limitation a microcontroller, microprocessor, digital signal processor (DSP) and/or system on a chip (SoC) as described in this disclosure. System 100 may include, be included in, and/or communicate with a mobile device such as a mobile telephone or smartphone. System 100 may include a single computing device operating independently, or may include two or more computing devices operating in concert, in parallel, sequentially or the like; two or more computing devices may be included together in a single computing device or in two or more computing devices. System 100 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. System 100 may include one or more computing devices dedicated to data storage, security, distribution of traffic for load balancing, and the like. System 100 may distribute one or more computing tasks as described below across a plurality of computing devices of computing device, which may operate in parallel, in series, redundantly, or in any other manner used for distribution of tasks or memory between computing devices. System 100 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. In a non-limiting embodiment, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 includes a display device 112 wherein display device 112 displays a graphical user interface 116. A "graphical user interface," as used herein, is a graphical form of user interface that allows users to interact with electronic devices. In some embodiments, GUI 116 may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages, and the like may be represented using a small picture in a graphical user interface. In a non-limiting embodiment, links to decentralized platforms as described in this disclosure may be incorporated using icons. Using an icon may be a fast way to open documents, run programs etc. because clicking on them yields instant access.

As used in this disclosure, an "interactive element" is a component within a system, interface, or device that allows a user to engage with and influence the system's behavior or output through actions. In a non-limiting example, the actions may include clicking, touching, or inputting data. Without limitation, the interactive element 120 may respond dynamically to an input, enabling real-time feedback or control over system functions. In a non-limiting embodiment, without limitation the interactive element 120 may include buttons, sliders, input fields, or menus in software interfaces, as well as physical controls like switches or touchscreens in hardware devices. Each interactive element of a plurality of interactive elements May comprise an event handler configured to detect an interaction and generate response data as a function of the interaction.

As used in this disclosure, a "visual element" is a component or feature within a system, display, or interface that conveys information through visual means. In a non-limiting example, the plurality of visual elements 124 may include text, images, icons, shapes, colors, and/or other graphical components designed to be perceived by the user. In a non-limiting example, the plurality of visual elements 124 may aid in communication, navigation, and/or interaction with the system. Without limitation, the plurality of visual elements 124 may be used to enhance user experience, guide behavior, and/or represent data visually in an intuitive or informative way. The plurality of visual elements 124 may include any data transmitted to display device, client device, and/or graphical user interface 116. In some embodiments, the plurality of visual elements 124 may be interacted with. In a non-limiting embodiment, the plurality of visual elements 124 may include an interface, such as a button or menu. In some embodiments, the plurality of visual elements 124 may be interacted with using a user device such as a smartphone, tablet, smartwatch, or computer.

Still referring to FIG. 1, processor 104 displays, using the graphical user interface 116 a plurality of command input event handlers 128 wherein a command 132 in the plurality of command input event handlers 128 corresponds to the plurality of visual elements 124. As used in this disclosure, a "command input event handler" is a is a structured list of tasks, instructions, and/or operations that are organized in a specific sequence. In a non-limiting example, the plurality of command input event handlers 128 may include at least a command 132. As used in this disclosure, a "command" is an instruction or directive given to a person, system, device, and/or process to perform a specific action or task. Without limitation, the command 132 may initiate an operation, alter system behavior, or trigger a response, and may be issued manually by a user or automatically by a program or system. In a non-limiting example, the command 132 may control hardware functions, execute software routines, or interact with external systems, and may be part of a sequence within the plurality of command input event handlers 128. In a non-limiting example, the command 132 may be awaiting execution or confirmation from a user. In a non-limiting example, the plurality of command input event handlers 128 may function as a checklist where each command 132 or task may be processed, executed, or marked as completed by the user or system.

Continuing reference to FIG. 1, at least a processor 104 may be configured to generate a display data structure 136. As used herein, a "display data structure" refers to an organized framework of data that resides in the memory of a computing device and is configured to represent various metrics visually within a graphical user interface (GUI). The display data structure may include elements that define the positioning, styling, and interactivity of graphical components, enabling a dynamic visualization of statuses. In an embodiment, display data structure 136 may be configured to represent various patient therapy metrics visually within GUI 116. For example, the display data structure may contain conditional logic that updates the color-coding of each patient's visual representation based on therapy completion thresholds (e.g., green if therapy is fully administered, yellow if partially administered, and red if not administered). Additionally, the display data structure may support sorting and filtering features to organize patient entries according to unadministered therapy amounts or other customizable parameters, providing an intuitive, real-time view for clinical staff to monitor and manage patient therapy requirements effectively.

Continuing reference to FIG. 1 generating the display data structure 136 may include providing the plurality of visual elements 124 and at least an event handler 128. In an embodiment, the plurality of visual elements 124 may represent distinct patient therapy statuses and metrics. Specifically, the visual elements 124 may include color-coded indicators, icons, or text fields that display each patient's therapy status, allowing clinicians to quickly assess whether a patient's therapy has been fully, partially, or not administered, based on predefined thresholds. Each visual element 124 may be linked to data fields that represent individual patient therapy metrics, enabling the elements to dynamically update in response to changes in therapy data. At least an event handler 128 may be integrated into the display data structure 136 to respond to user interactions, such as clicking or tapping on a patient's entry to reveal more detailed information, sorting patient entries by therapy status, or filtering by specific therapy types. At least an event handler 128 may facilitate real-time updates to the GUI, ensuring that any modifications to patient therapy data are immediately reflected in the visual display.

Continuing reference to FIG. 1, generating the display structure 136 may include linking a first visual element 140 to execution sequence data 144. As used herein, "execution sequence data" refers to structured data that captures the chronological order, type, and parameters of actions or events executed within a system. Execution sequence data 144 May include timestamped entries of each action, identifiers for specific event types, and associated quantitative or qualitative metrics that detail the scope or intensity of each executed action. This data structure allows for the sequential logging and retrieval of event information, supporting real-time analysis, verification, and monitoring of the execution process. In an embodiment, execution sequence data 144 may refer to data that records the sequence, type, and amount of therapy administered to a patient over a specified time period, in alignment with the patient's prescribed treatment plan. Execution sequence data 144 may include time-stamped entries of each administered therapy session, the type of therapy performed (e.g., physical, occupational, or speech therapy), and the duration or intensity of each session. In an embodiment, execution sequence data 144 may include specific execution sequence data 148. As used herein, "specific execution sequence data" refers to a subset of execution sequence data that is directly associated with a single entity or subject within the system, such as an individual user or object. This specific execution sequence data 148 may include detailed, individualized records that capture the chronological sequence, type, and parameters of actions executed exclusively for that entity. In a non-limiting embodiment, in the case of a healthcare or rehabilitation application, specific execution sequence data 148 may encompass the individual entries of actions administered to a single patient, including time-stamped entries, types of actions or events, and metrics associated with each action, such as duration, intensity, or adherence to a defined protocol.

As used herein, a "first visual element" refers to a graphical component within the GUI, as an icon, progress bar, or color-coded status indicator, that visually represents the execution sequence data. In an embodiment, the first visual element 140 may display as a green indicator if the execution sequence data shows the patient has received the full prescribed therapy for the day, a yellow indicator if therapy is partially completed, or a red indicator if no therapy has been administered. By linking the first visual element 140 to execution sequence data, the system can dynamically update the visual representation in real-time as new therapy sessions are logged. In an embodiment, first visual element 140 may include a chatbot feature. As used herein, a "chatbot interface" refers to a user interface that allows users to interact with system 100 through natural language input, typically in the form of text or speech. In an embodiment, the chatbot interface 152 enables users to issue queries, provide commands, or make specific requests, to which system 100 is configured to respond with relevant data or actions. The chatbot interface 152 may utilize Natural Language Processing (NLP) to interpret and process the user's input. NLP is a subfield of artificial intelligence focused on enabling computers to process, understand, and generate human language. NLP systems consist of multiple layers of text analysis, including tokenization (breaking down a query into individual components such as words or phrases), part-of-speech tagging (identifying grammatical elements in the query), syntactic parsing (understanding sentence structure), and semantic analysis (extracting the meaning and intent behind the query). In an embodiment, the chatbot interface 152 may incorporate advanced NLP techniques, such as word embeddings (e.g., Word2Vec, GloVe), which map words to vector representations to capture context and meaning, as well as transformer-based architectures (e.g., BERT, GPT), which allow the system to handle more complex queries that depend on contextual relationships between words. Additionally, the system 100 may apply entity recognition to identify key elements within the first projection structure (e.g., patient names, medical terms, statistics) and intent recognition to classify the purpose of the first projection structure (e.g., requesting information, making a decision, performing an action). Upon processing the first projection structure, system 100 may use these NLP models to update execution sequence data 144, which could include retrieving structured data from databases (e.g., patient therapy recommendations, improvement statistics, etc.). Through the chatbot interface 152, users can seamlessly interact with system 100, which leverages NLP to intelligently understand, process, and respond to queries in real time.

Continuing reference to FIG. 1, in an embodiment, at least a processor 104 may be configured to wherein the at least a processor is further configured to calculate a predicted execution sequence completion time for the specific execution sequence data as a function of cluster execution sequence data and real-time execution sequence data; and display, using the graphical user interface, the predicted execution sequence completion time. As used herein, "cluster execution sequence data" refers to aggregated data on execution sequences across groups that show common patterns within demographic cohorts. Cluster execution sequence data may capture cohort-based trends and behaviors. The processor may reference cluster execution sequence data, which may include historical data from cases or patient cohorts sharing similar treatment protocols, conditions, and adherence characteristics, establishing a baseline for typical completion times. The at least a processor 104 may then integrate real-time execution sequence data, capturing the patient's ongoing adherence to and progression through the prescribed actions. This integration may allow the at least a processor 104 to adjust a predicted completion time to reflect current adherence, frequency, or session durations. The processor may then display the calculated predicted execution sequence completion time within the GUI 116, where it may appear as a timeline, progress bar, countdown, or similar visual representation to reflect the estimated completion time based on the combined data inputs. In an embodiment, at least a processor 104 may be configured to assign a priority ranking to the predicted execution sequence completion time, where the priority ranking may prioritize certain tasks within the execution sequence data to ensure that a patient aligns with their current treatment plans. This prioritization may be based on various factors, such as the urgency, clinical significance, or adherence level required for each task to ensure alignment with the patient's current treatment plan. The at least a processor 104 may analyze individual tasks within the execution sequence data 144, assigning higher priority rankings to those deemed critical for achieving treatment goals within the predicted timeframe, while assigning lower rankings to less time-sensitive actions. A machine learning model may be used to generate a "priority score" to assist with ranking the tasks. In some embodiments, the machine-learning model may be trained on historical data where tasks may be correlated with priority scores. This model can be retrained over time with user feedback, refining its prioritization based on real-world outcomes. This prioritization process may also leverage a natural language processing (NLP) or large language model (LLM) trained on a corpus of medical literature, helping it learn which therapies or interventions are commonly prioritized in clinical settings. For example, NLP or LLM models may be configured to identify sentiment data for tokens extracted from medical literature. For the purposes of this disclosure, "Sentiment data," is data concerning the approval or disapproval of a therapy evidenced by the medical and/or scientific literature. Such a model may either assign a priority score to individual tasks or produce a fully prioritized execution sequence, aligning with best practices noted in medical literature.

With continued reference to FIG. 1, generating the display structure 136 may include linking a second visual element 156 to action sequence data 160. As used herein, "action sequence data" refers to structured data that details the prescribed or planned series of actions to be executed according to a defined protocol or set of guidelines. This data may include ordered entries specifying types of actions, intended frequency, duration, or other parameters that establish the expected sequence for achieving a particular outcome or goal. In an embodiment, action sequence data 160 may include to data that encapsulates the therapist's prescribed recommendations or planned sequence of therapeutic actions for a patient, such as the patient indicated in specific execution sequence data 148. This data includes specific therapy types, frequencies, durations, and intensity levels that align with the therapist's assessment and treatment goals for the patient. For example, action sequence data may define that a patient should receive specific therapies, such as physical or occupational therapy, with designated session durations and frequency, ensuring alignment with best practices for patients of similar profiles or diagnoses. Action sequence data thus may serve as the baseline or intended therapeutic plan, against which actual administered therapy (execution sequence data) is compared. By linking a second visual element to this action sequence data, the GUI may visually indicate if the administered therapy is meeting, partially meeting, or deviating from the therapist's recommended plan, enabling clinical staff to monitor adherence to prescribed therapy sequences and quickly address any discrepancies. In an embodiment, second visual element 156 may include a second chatbot feature 164. This second chatbot feature 164 may allow users, such as clinicians or therapists, to quickly access or review specific action sequence data, i.e., therapist-recommended treatment plans, by interacting directly with the system through natural language queries or prompts. The second chatbot feature 164 could offer various functionalities, such as answering user inquiries regarding a patient's recommended therapy plan, suggesting adjustments based on real-time therapy completion data, or providing reminders and alerts for therapy actions that remain uncompleted. Additionally, the chatbot may use predefined responses or access to real-time patient data to address routine questions, such as "What therapy is remaining for this patient today?" or "Has the patient received the required physical therapy session?" and the like.

Still referring to FIG. 1, generating the display structure 136 may include verifying the action sequence data 160 using a verification module 168. As used herein a "verification module" refers a component within the system that cross-references the action sequence data against predefined standards, criteria, or datasets to assess the accuracy and consistency of the action sequence data. The verification module 168 may analyze individual elements of the action sequence data 160-such as therapy type, frequency, and duration- and compare them to therapeutic guidelines, best practices, or similar patient data across a cohort with comparable characteristics. The verification module 168 may also identify any discrepancies, redundancies, or deviations in the therapist's recommendations, providing real-time feedback on the action sequence data 160 before or during execution. This functionality helps ensure that each patient's treatment plan aligns with evidence-based practices and that it accounts for specific patient needs, thereby improving consistency and quality of care. In addition, the verification module may automatically flag any outliers or unusual patterns in action sequence data, prompting further review by clinical staff. This verification process supports continuous accuracy in therapy recommendations, enhancing the overall effectiveness of the display structure by ensuring that displayed recommendations are reliable and patient-appropriate. In an embodiment, the verification module 168 may be configured to compare the action sequence data 160 related to specific execution sequence data 148 with action sequence data associated with a cluster of execution sequence data, wherein the cluster of execution sequence data has at least one shared characteristic with the specific execution sequence data. This shared characteristic may include demographic or diagnostic features, such as age, medical condition, therapy type, or treatment stage, that align the specific execution sequence data with a comparable group or cohort. Through this comparison, the verification module 168 may evaluate the appropriateness and effectiveness of the therapist's recommendations by assessing whether the action sequence data 160 aligns with typical therapy patterns or outcomes observed within the relevant cluster. For example, if the specific execution sequence data pertains to a patient recovering from a particular type of injury, the verification module may compare the therapist's recommendations against action sequence data for other patients with similar injuries. This enables the verification module to identify any deviations from standard practice or flag recommendations that fall outside typical therapeutic parameters for the cluster. In an embodiment, if the verification module 168 determines that the action sequence data 160 does not align with the general action sequence data associated with the cluster of execution sequence data, a notification may be generated through the second visual element 156, indicating that a follow-up action is required. This notification may alert clinical staff to potential discrepancies in the recommended therapy plan, prompting a review or adjustment to ensure alignment with best practices or standards observed within the comparable cohort. The notification generated by the second visual element 156 may provide actionable insights, such as recommending a consultation with the therapist or suggesting alternative therapy parameters. In an embodiment, verification module 168 may include a verification machine-learning model 172 trained using verification training data. This verification training data may correlate example execution sequence data with verified action sequence data, historical action sequence data with verified counterparts, and example execution sequence data associated with verification statuses. Additionally, the training data could include execution sequence data correlated to outlier data, allowing the model to identify potential issues with unverified sequences. A cohort classifier could also be incorporated to classify the execution sequence data or patient data into groups with similar characteristics. This classification could be achieved using supervised or unsupervised methods, such as clustering algorithms, to group patients based on shared traits. To further enhance accuracy, multiple versions of the verification machine-learning model 172 could be trained on cohort-specific datasets.

In an embodiment, the GUI 116 may be modified using an interface simulator. As used herein, an "interface simulator" is a component specifically configured to adjust the plurality of visual elements 124 within the GUI based on a comparison between the execution sequence data 144 and the action sequence data 160. This interface simulator may monitor discrepancies, alignments, or deviations between the actual actions recorded in the execution sequence data and the prescribed actions outlined in the action sequence data. For example, if the interface simulator detects that the execution sequence data 144 is only partially aligned with the action sequence data 160, it may adjust the visual parameter of a progress indicator to yellow, signaling partial completion. If a substantial misalignment is detected, it might adjust the indicator to red or even trigger additional visual or textual notifications. The interface simulator may be generated using an interface simulator machine learning model trained with historical training data that correlates execution sequence data and action sequence data with comparison values. In this model, the comparison values may be generated by analyzing differences between actual execution sequences—capturing real-world actions specific to patient characteristics—and the ideal action sequences, which reflect best practice treatment protocols. These comparison values may indicate the degree of alignment or deviation between real-world actions and recommended practices. The comparison values may serve as a foundation for generating alerts, notifications, or recommendations within the system. For example, if a significant deviation is detected between a patient's execution sequence and the best practice protocol, an alert could be triggered to prompt a review or intervention.

With continued reference to FIG. 1, generating the display data structure 136 may include generating adjusted execution sequence data 170 as a function of the verified action sequence data 160. As used herein, "adjusted execution sequence data" refers to execution sequence data that has been modified or recalibrated to align with verified action sequence data or recommended protocols. In an embodiment, adjusted execution sequence data 170 may reflect modifications to the execution sequence data 144, such as recalibrating therapy types, frequencies, or durations to align with verified standards or to correct any deviations from the prescribed plan. In an embodiment, if the verified action sequence data 160 indicates that a patient requires a certain therapy more frequently than originally instructed, the adjusted execution sequence data 170 may be updated to reflect this increased frequency. Alternatively, if certain therapeutic actions are deemed unnecessary or ineffective based on the verification, they may be minimized or removed in the adjusted data. In an embodiment, adjusted execution sequence data 170 may provide a real-time, refined representation of the patient's ongoing therapy plan, allowing clinical staff to view and administer therapy that remains responsive to individualized recommendations identified within specific execution sequence data 148. In an embodiment, generating adjusted execution sequence data may include generating an adjusted execution sequence machine learning model trained using adjusted execution sequence training configured to correlate adjusted execution sequence data to example or historical verified action sequence data. Other examples of inputs into the adjusted execution sequence training data may include verification modules, specific execution sequence data, user feedback, previous iterations of adjusted execution sequence machine-learning model outputs, and the like.

With continued reference to FIG. 1, generating the display data structure 136 may include classifying the adjusted execution sequence data to a status 176 using a classifier 180. As used herein, a "status" refers to a categorization assigned to the adjusted execution sequence data that indicates the patient's adherence to the prescribed treatment plan. In an embodiment, status 176 may reflect whether the patient is "on track," "partially on track," or "off track" based on the extent to which the administered therapies align with the verified action sequence data. In a non-limiting embodiment, if the adjusted execution sequence data 170 indicates that the patient has received all prescribed treatments as recommended, the classifier may assign a status of "on track." Conversely, if some treatments are missed or administered inconsistently with the prescribed schedule, the status may be marked as "partially on track" or "off track." The status 176 may also be indicated through use of a color scheme, with green being on track, yellow being partially on track, and red being off track. The status 176 may be indicated in any way as discussed throughout the entirety of this disclosure. In an embodiment, classifying the adjusted execution sequence data 170 to a status 176 may include classifier 180. Classifier 180 may be configured to correlate adjusted execution sequence to a status using training data comprising historical status correlations, example status correlations and the like. Classifier 180 may employ the use of status machine-learnings models to make connections and correlations. Classifier 180 may be consistent with any classifier or machine-learning process discussed throughout this disclosure. In an embodiment, generating the display data structure may include generating real-time alerts triggered by associated statuses. These real-time alerts may be configured to notify users when specific conditions or limits within the adjusted execution sequence data are reached, such as adherence levels dropping below a required percentage or a task remaining incomplete beyond a set time frame. The graphical user interface (GUI) may also incorporate a filter option that allows users to sort specific execution sequence data based on status, such as "completed," "in progress," or "pending." This filtering capability enables users to view task data organized according to their current state, allowing for quick identification and review of tasks at various completion stages. In an embodiment, the GUI 116 may include drag-and-drop functionality that allows users to adjust the status 176 of a task directly within the interface. By dragging and dropping tasks to different status categories, users can update progress markers or completion levels interactively. This adjustment automatically updates the third visual element, reflecting the new status 176 in real-time and ensuring that the display structure accurately represents the most current state of task completion.

With continued reference to FIG. 1, generating the display data structure 136 may include linking a third visual element 184 to the status 176. As used herein a "third visual element" refers to a visual element tied with the indication of a status 176 category. Third visual element 184 may be represented through an interactive graph, chart, text box, response structure and the like. In an embodiment, the third visual element 184 may include detailed contextual information that provides insight into the reasons behind the assigned status 176. In an embodiment, if the status reflects that the patient is "off track," the third visual element might display contributing factors, such as missed therapy sessions or deviations from prescribed treatment durations. Third visual element 184 may also offer recommended remedial actions, such as rescheduling missed sessions or adjusting treatment intensity to bring the patient back on track. Furthermore, the third visual element 184 may include historical data related to the patient's adherence trends.

With continued reference to FIG. 1, at least a processor 104 may be configured to generate the display data structure 136 using the plurality of visual elements 124 and the at least an event handler 128. This configuration may involve arranging and linking each visual element—such as the first, second, and third visual elements—to the underlying data, enabling them to accurately represent different aspects of patient treatment status, therapy adherence, and recommended actions. The processor 104 may also configure the at least an event handler 128 to respond to user interactions, allowing clinical staff to click, hover over, or select elements to access detailed information, historical data, or suggested actions.

With continued reference to FIG. 1, at least a processor 104 may configure, using the display data structure 136, the display device 112, to display the display data structure 136. This process may include translating the display data structure 136 into a visual layout on the display device 112, with each visual element positioned and styled according to the GUI design. The processor 104 may ensure that all linked data and status updates are accurately rendered on the display device 112. Additionally, the processor 104 may manage real-time updates to the display, ensuring that any changes in execution sequence data, action sequence data, or status are immediately reflected within the visual interface.

Figure 2A:
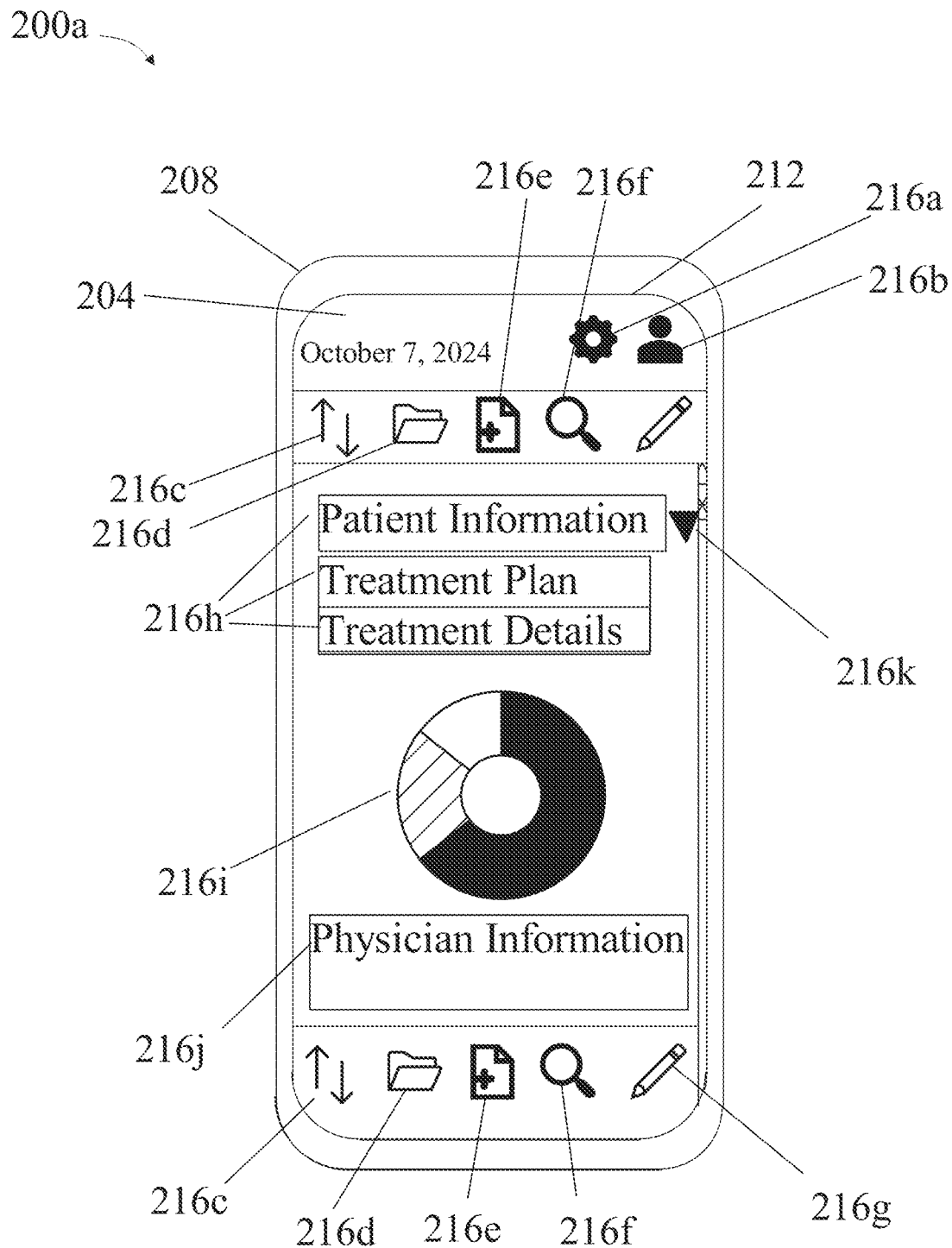
FIG. 2A is an exemplary illustration of an execution sequence data displayed within graphical user interface.

Referring now to FIG. 2A, an exemplary illustration 200a of an execution sequence data displayed within graphical user interface. In an embodiment, the graphical user interface 204 may be displayed using a downstream device 208. In an embodiment, the graphical user interface 204 may include at least a visual element 212. In an embodiment, the visual element 212 may include an interactive element 216. In an embodiment the interactive element 216 may allow a user to engage directly with the graphical user interface 204 through a variety of actions.

In an embodiment, the interactive element 216a-i may include a settings gear 216a, a profile icon 216b, a sorting icon 216c, a folder 216d, a new task icon 216e, a find icon 216f, an edit icon 216g, a check box icon 216h, a scroll bar 216i, text description 216j, and the like.

In an embodiment, the interactive element 216 may include a settings gear 216a. In an embodiment, the settings gear 216a may enable users to access the system or application settings where they may modify preferences and configurations. Without limitation, by clicking on the settings gear 216a, users may adjust features like notifications, display options, account details, and the like. In an embodiment, the settings gear 216a may represent control over personalizing the environment within the application. In an embodiment, the settings gear 216a may ensure that users can customize their experience to meet their specific needs.

In an embodiment, the interactive element 216 may include a profile icon 216b, which may allow users to access their personal profile settings. In an embodiment, the profile icon 216b may link to a page where users may view and edit their personal information, such as their name, contact details, or profile picture. In an embodiment, the profile icon 216b may make it simple for users to manage their account and view related data quickly. In an embodiment, the profile icon 216b may be placed in a convenient location, allowing easy access to account settings. In an embodiment, the profile icon 216b may help users maintain control over their profile, ensuring that their information stays up-to-date.

In an embodiment, the interactive element 216 may include a sorting icon 216c, which may allow users to organize data based on specific criteria. In an embodiment, the sorting icon 216c may be useful when dealing with large datasets or lists that need to be filtered or reordered. Without limitation, by clicking the sorting icon 216c, users may arrange items by various attributes such as date, name, priority, and the like. In an embodiment, the sorting icon 216c may simplify the process of locating specific information, making the interface more efficient to use. In an embodiment, the sorting icon 216c may ensure that users can easily customize how they view and interact with the content.

In an embodiment, the interactive element 216 may include a folder icon 216d, which may represent access to a file or document management system. Without limitation, by clicking on the folder icon 216d it may open a directory or list of stored files, allowing users to organize their content within the application. In an embodiment, the folder icon 216d may be essential for managing documents, media, or other file types efficiently. In an embodiment, the folder icon 216d may be associated with file storage and navigation, making it a familiar and intuitive tool for users. In an embodiment, the folder icon 216d may aid in keeping information organized and accessible within the system.

In an embodiment, the interactive element 216 may include a new task icon 216e, which may allow users to create or add a new item to their task list or project. In an embodiment, the new task icon 216e may provide a quick way for users to input new assignments or goals, streamlining task management. In an embodiment, the new task icon 216e once clicked, May open a form or prompt where users may specify details about the new task. In an embodiment, the new task icon 216e may help users stay organized by adding tasks efficiently as they arise. In an embodiment, the new task icon 216e may be a valuable tool for productivity, helping users keep track of their to-do lists.

In an embodiment, the interactive element 216 may include a find icon 216f, which may function as a search tool for locating specific information within the application. In an embodiment, the find icon 216f may allow users to quickly search through data, files, or content to pinpoint exactly what they need. In an embodiment, the find icon 216f may be especially useful in applications that manage large volumes of information or files. In an embodiment, the find icon 216f may enhance efficiency by reducing the time spent manually browsing through content. Continuing, by providing a fast search function, users may access information more quickly and effectively.

In an embodiment, the interactive element 216 may include an edit icon 216g, which may enable users to modify or update existing content within the application. Continuing, by clicking on the edit icon 216g, it may bring users to an editable version of the item, such as a text document, task, or file. In an embodiment, the edit icon 216g may allow users to make corrections or updates as needed, maintaining the accuracy of the information. In an embodiment, the edit icon 216g may ensure that content remains current and can be easily adjusted as situations or data change. In an embodiment, the edit icon 216g may be a crucial tool for users who frequently update or revise their work.

Continuing reference to FIG. 2A, interactive element 216h may include information pertaining to a execution sequence data corresponding to specific execution sequence data. This interactive element may initially display a prompt box or placeholder text, giving users an overview or hint of the available information. Upon interaction, such as when the user clicks, taps, or hovers over the interactive element, the placeholder text may automatically disappear, making way for a detailed display of additional information. Once activated, interactive element 216h may dynamically expand or transition to reveal more comprehensive data, including information that identifies and details the execution sequence data. The execution sequence data may encompass various data points related to the specific execution sequence data, such as diagnosis, previous health treatment plans, usage of hospital resources, and the like. The displayed information could include a breakdown of time intervals, statistical summaries, or graphical representations that enable users to understand the relationship between the patient's actual hospital stay and the expected or allowable duration. The interaction with element 216h may be enhanced by context-sensitive animations or transitions that guide the user's attention from the placeholder prompt to the expanded information view, ensuring a smooth and engaging user experience. Additionally, the element may be designed to display tooltip descriptions, expandable sections, or hover-over details that provide further clarity about each data subset in the projection structure, allowing users to explore data progressively without overwhelming them with too much information at once. Interactive element 216h may include a chatbot feature allowing users to enter queries or retrieve responses from system 100. These visual cues may improve interpretability and provide a more intuitive understanding of complex datasets. A dropdown icon 216k allows users to expand the first data, to provide more in-depth diagnosis, patient history, or other relevant data. By selecting this dropdown icon, users may access layered data without leaving the current interface, ensuring that critical contextual information is readily available.

Continuing reference to FIG. 2A, interactive element 216i includes a visual representation of the execution sequence data. In an embodiment, interactive element 216i may include a graphical or diagrammatic representation of the execution sequence data. In an embodiment, a shaded portion of a diagrammatic representation may represent the current progress related to the execution sequence plan, whereas a non-shaded portion may represent a typical treatment plan, for patients with similar demographics. The partly shaded portion of interactive element 216i may represent the projected amount of time that a patient will stay at the facility to continue treatment. The representation could be generated in real-time based on the plurality of inputs and may display various types of data, such as text summaries, charts, tables, or other visual representations of the system's response. The interactive element 216i may be interactive, allowing users to engage with the displayed information. For instance, users could click on specific elements within the diagrammatic representation, such as data points on a chart or text segments, to request additional details, perform follow-up actions, adjust node utilization interval, and the like. This interactive nature enables the response structure to serve not only as a display for the system's output but also as a hub for further user interaction, driving the flow of information based on evolving plurality of inputs. In some embodiments, the diagrammatic representation may be designed to dynamically update in response to changes in the plurality of inputs or the system's internal state. For example, if the user submits modifies parameters of the first data, the diagrammatic representation could be automatically refreshed to reflect the new data. The graphical elements within the structure, such as charts or tables, may be reconfigured to highlight relevant information or present new insights derived from the updated input.

Continuing reference to FIG. 2A, interactive element 216j functions as a response structure, designed to prompt the user to input specific data related to the action sequence data. This interactive element may present users with a form, dialog box, or selection field where they can enter details such as treatment type, frequency, duration, or other parameters relevant to the recommended action sequence. For example, interactive element 216j may display predefined options for therapy types, allowing clinical staff to quickly select or adjust therapy recommendations to align with the patient's needs. Additionally, this response structure may guide the user through required inputs, prompting them to confirm or modify action sequence data based on real-time observations or updates from the therapy session. Interactive element 216j may also validate entries to ensure compliance with established protocols or guidelines, providing alerts or feedback if the input deviates from expected values or best practices. The response structure's design may include dynamic features such as drop-down menus, radio buttons, or sliders, which streamline the data entry process and reduce the potential for user error. By integrating interactive element 216j into the GUI, the system ensures that action sequence data remains accurate and up-to-date, supporting the integrity of therapy recommendations and enabling responsive adjustments based on clinical input. Interactive element 216j may include a chatbot feature allowing users to enter queries or retrieve responses from system 100.

Figure 2B:
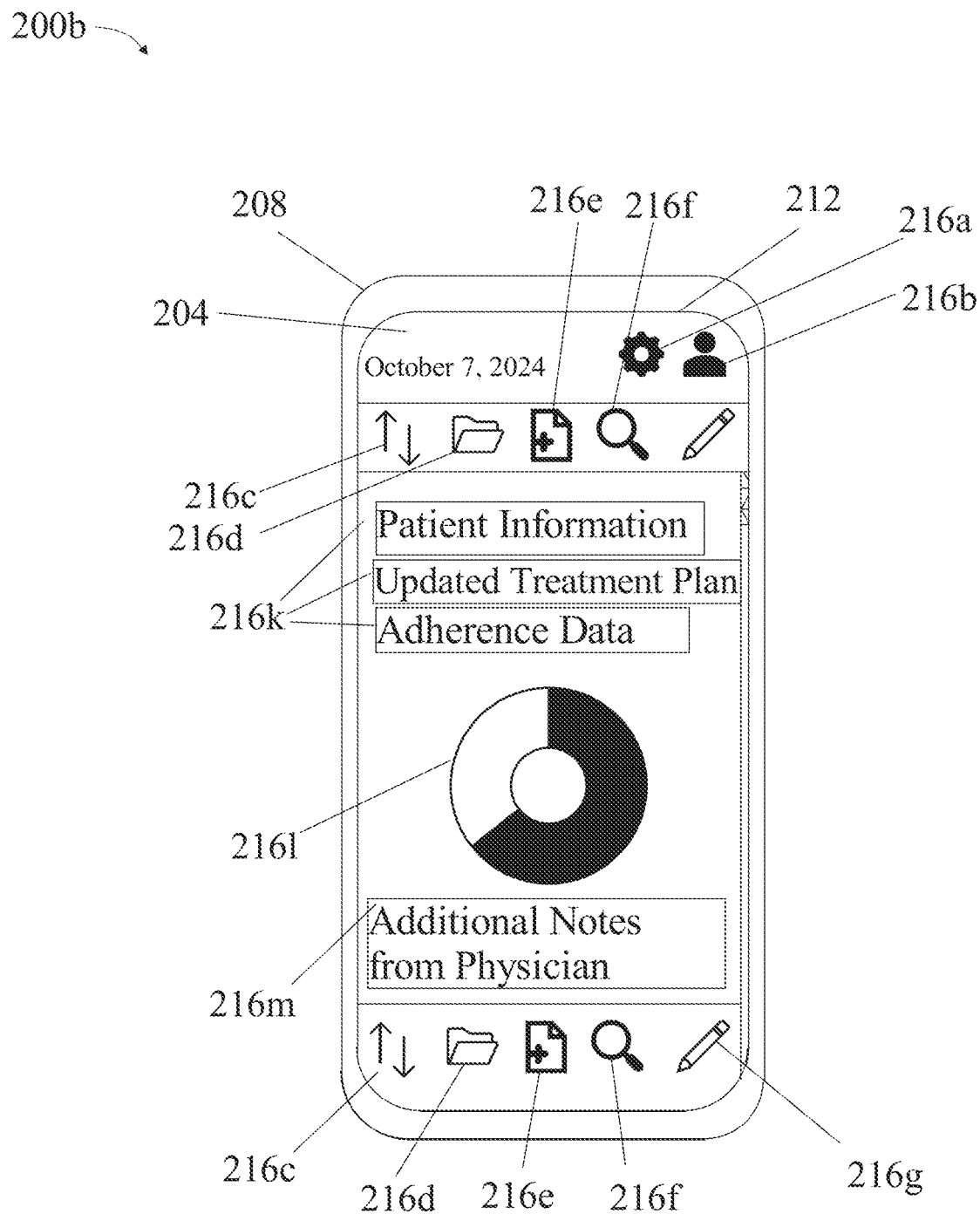
FIG. 2B is an exemplary illustration of a second projection structure in a graphical user interface.

Now referring to FIG. 2B, an exemplary illustration 200b of adjusted execution sequence data in graphical user interface is illustrated. Interactive element 216k may include information pertaining to the adjusted execution sequence data and relevant status. When the user clicks or taps on the prompt box, the placeholder text may disappear and display more information identifying the adjusted execution sequence data. Interactive element 216k may display an overview of the adjustments made to the execution sequence data, such as modifications to therapy frequency, intensity, or duration, which were applied to better align with verified action sequence data or to address identified discrepancies in treatment adherence.

In an embodiment, interactive element 216l may include a graphical or diagrammatic representation of the adjusted execution sequence data and relevant status. Interactive element 216l may include a graphical or diagrammatic representation of the adjusted execution sequence data and relevant status, providing users with a visual overview that highlights therapy adherence, adjustments, and progress within the prescribed treatment plan. This representation may take the form of charts, timelines, progress bars, or flow diagrams that illustrate the sequence and status of each therapy action in a clear and intuitive format. For instance, interactive element 216l might display a timeline showing each therapy session, color-coded to indicate adherence status-green for completed as planned, yellow for partially completed, and red for missed or incomplete sessions. Additionally, this element could use icons, markers, or symbols to visually differentiate between types of adjustments, such as increased frequency, modified intensity, or adjusted duration, making it easy for clinical staff to identify where and why changes have been implemented in the execution sequence. The graphical or diagrammatic display may also support interactive features, allowing users to hover over or click on specific data points to reveal additional information, such as timestamps, therapist notes, or recommendations associated with each therapy session. Interactive element 216l may also incorporate a circle graph, functioning as a progress wheel, to visually display the patient's adherence and completion of the adjusted execution sequence. This progress wheel could illustrate the percentage of therapy actions completed versus remaining, with segments color-coded to represent adherence status (e.g., green for completed as planned, yellow for partially completed, and red for missed or unexecuted actions). The circular format provides a quick, at-a-glance view of overall progress, helping clinical staff immediately assess whether the patient is on track with their prescribed therapy. In addition to showing overall completion, the circle graph may have segmented sections corresponding to different types or stages of therapy, allowing for a more detailed breakdown within the progress wheel. For instance, specific therapy types (e.g., physical therapy, occupational therapy) could be represented as individual segments within the circle, each tracking the status and completion rate of its associated tasks. Interactive features such as tooltips may appear when hovering over segments, offering more granular information on session timestamps, adjustments made, or therapist notes related to each portion of the therapy plan.

Continuing reference to FIG. 2B, Interactive element 216m may be configured to display information related to action sequence data. In an embodiment, interactive element 216m may include information such as physician notes, treatment progress, treatment notes and the like. Initially, this element may appear as a prompt box with placeholder text briefly indicating its purpose. When the user engages with interactive element 216m by clicking or tapping, the placeholder text disappears, revealing a more comprehensive view of the action sequence plan and related information.

Figure 3:
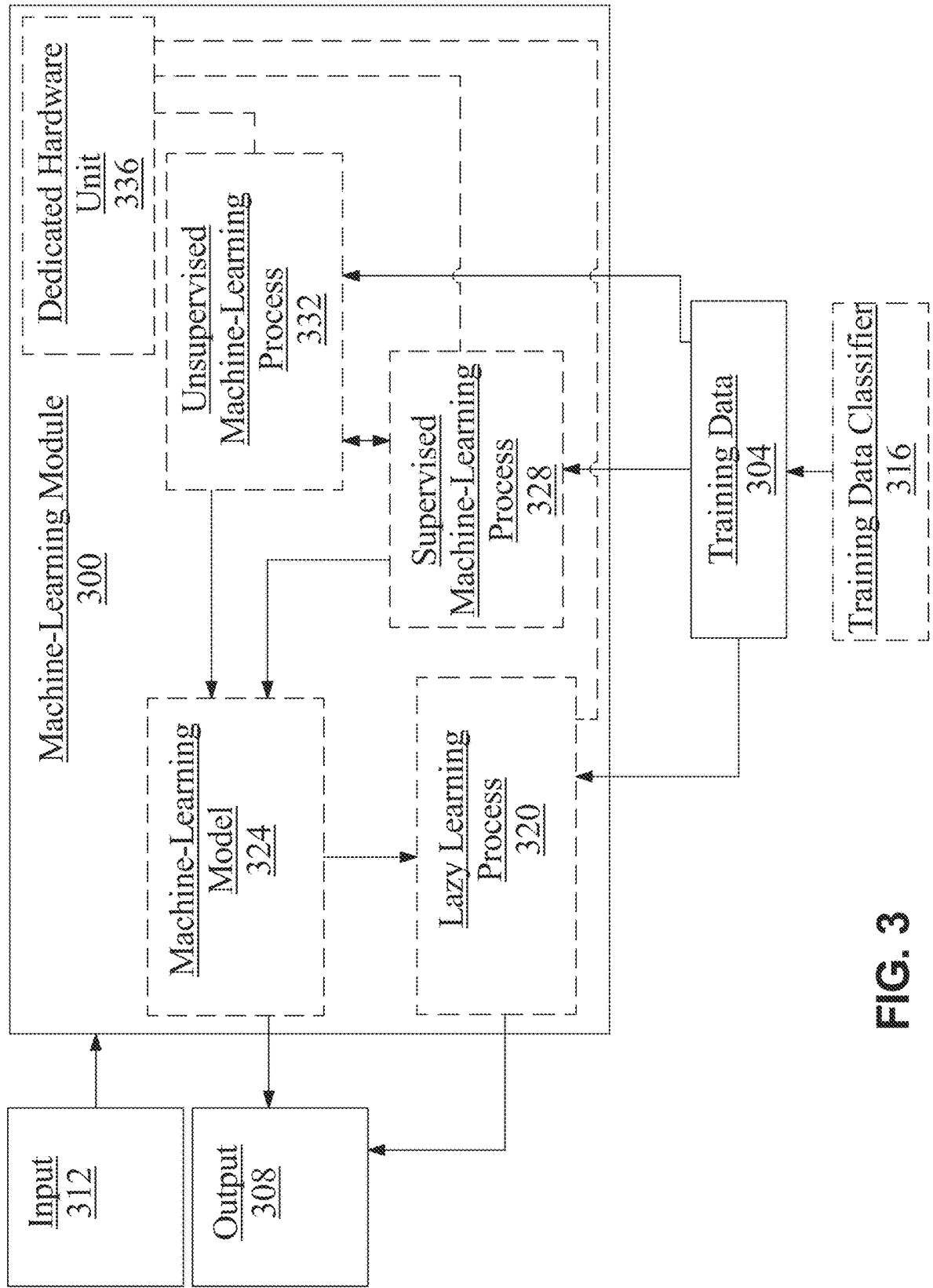
FIG. 3 is a block diagram of an exemplary machine-learning process.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. In a non-limiting embodiment, and without limitation, training data 304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; In a non-limiting embodiment, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, In a non-limiting embodiment by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; In a non-limiting embodiment, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, in a non-limiting embodiment, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example inputs such as user input and plurality of command input event handlers and outputs such as optimization datum.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to categories of historical reference data and categories of historical plurality of command input event handlers.

Still referring to FIG. 3, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B) = P(B/A) P(A) = P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 3, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. In a non-limiting embodiment, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 3, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, in a non-limiting embodiment, be advantageous where cases represented in training data are represented by different quantities of samples, which may result in proportionally equivalent vectors with divergent values.

With further reference to FIG. 3, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. In a non-limiting embodiment, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, in a non-limiting embodiment, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 3, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 3, computer, processor, and/or module may be configured to sanitize training data. "Sanitizing" training data, as used in this disclosure, is a process whereby training examples are removed that interfere with convergence of a machine-learning model and/or process to a useful result. In a non-limiting embodiment, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, In a non-limiting embodiment, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 3, images used to train an image classifier or other machine-learning model and/or process that takes images as inputs or generates images as outputs may be rejected if image quality is below a threshold value. In a non-limiting embodiment, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 3, computing device, processor, and/or module may be configured to precondition one or more training examples. In a non-limiting embodiment, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. In a non-limiting embodiment, a computing device, processor, and/or module may convert a smaller number of units, such as in a low pixel count image, into a desired number of units, In a non-limiting embodiment by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 3, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, In a non-limiting embodiment by an N-sample compressor implemented using hardware or software. Anti-aliasing and/or anti-imaging filters, and/or low-pass filters, may be used to clean up side-effects of compression.

Further referring to FIG. 3, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, In a non-limiting embodiment as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $X_{max}$:

$$X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the 25th percentile value and the 50th percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 3, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, In a non-limiting embodiment using deep neural networks and/or generative adversarial networks; generative processes may be referred to alternatively in this context as "data synthesis" and as creating "synthetic data."

Augmentation may include performing one or more transformations on data, such as geometric, color space, affine, brightness, cropping, and/or contrast transformations of images.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. In a non-limiting embodiment, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. In a non-limiting embodiment, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. In a non-limiting embodiment, a supervised learning algorithm may include user input and plurality of command input event handlers as described above as inputs, optimization datum as outputs, and a scoring function representing a desired form of relationship to be detected between inputs and outputs; scoring function may, In a non-limiting embodiment, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

With further reference to FIG. 3, training a supervised machine-learning process may include, without limitation, iteratively updating coefficients, biases, weights based on an error function, expected loss, and/or risk function. In a non-limiting embodiment, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, In a non-limiting embodiment, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 3, a computing device, processor, and/or module may be configured to perform method, method step, sequence of method steps and/or algorithm described in reference to this figure, in any order and with any degree of repetition. In a non-limiting embodiment, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 332 may not require a response variable; unsupervised processes 332 may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 3, a machine-learning model and/or process may be deployed or instantiated by incorporation into a program, system, system and/or module. In a non-limiting embodiment, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, system, and/or method described in this disclosure; such examples may be modified and/or labeled according to user feedback or other processes to indicate desired results, and/or may have actual or measured results from a process being modeled and/or predicted by system, module, machine-learning model or algorithm, system, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like. Further referring to FIG. 3, one or more processes or algorithms described above may be performed by at least a dedicated hardware unit 336. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 336 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, In a non-limiting embodiment, including dedicated circuitry for matrix and/or signal processing operations that includes, e.g., multiple arithmetic and/or logical circuit units such as multipliers and/or adders that can act simultaneously and/or in parallel or the like. Such dedicated hardware units 336 may include, without limitation, graphical processing units (GPUs), dedicated signal processing modules, FPGA or other reconfigurable hardware that has been configured to instantiate parallel processing units for one or more specific tasks, or the like, A computing device, processor, system, or module may be configured to instruct one or more dedicated hardware units 336 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 4:
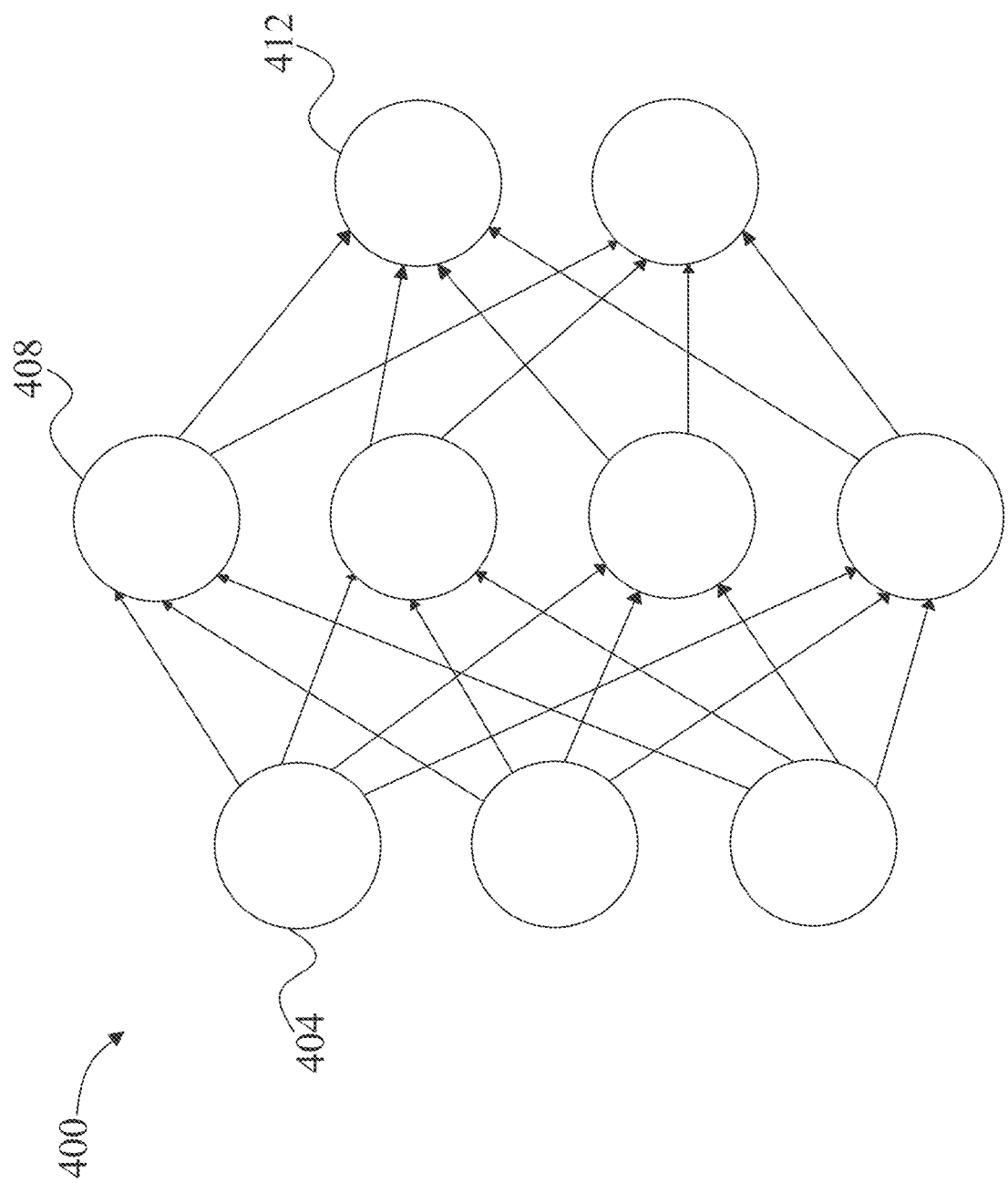
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
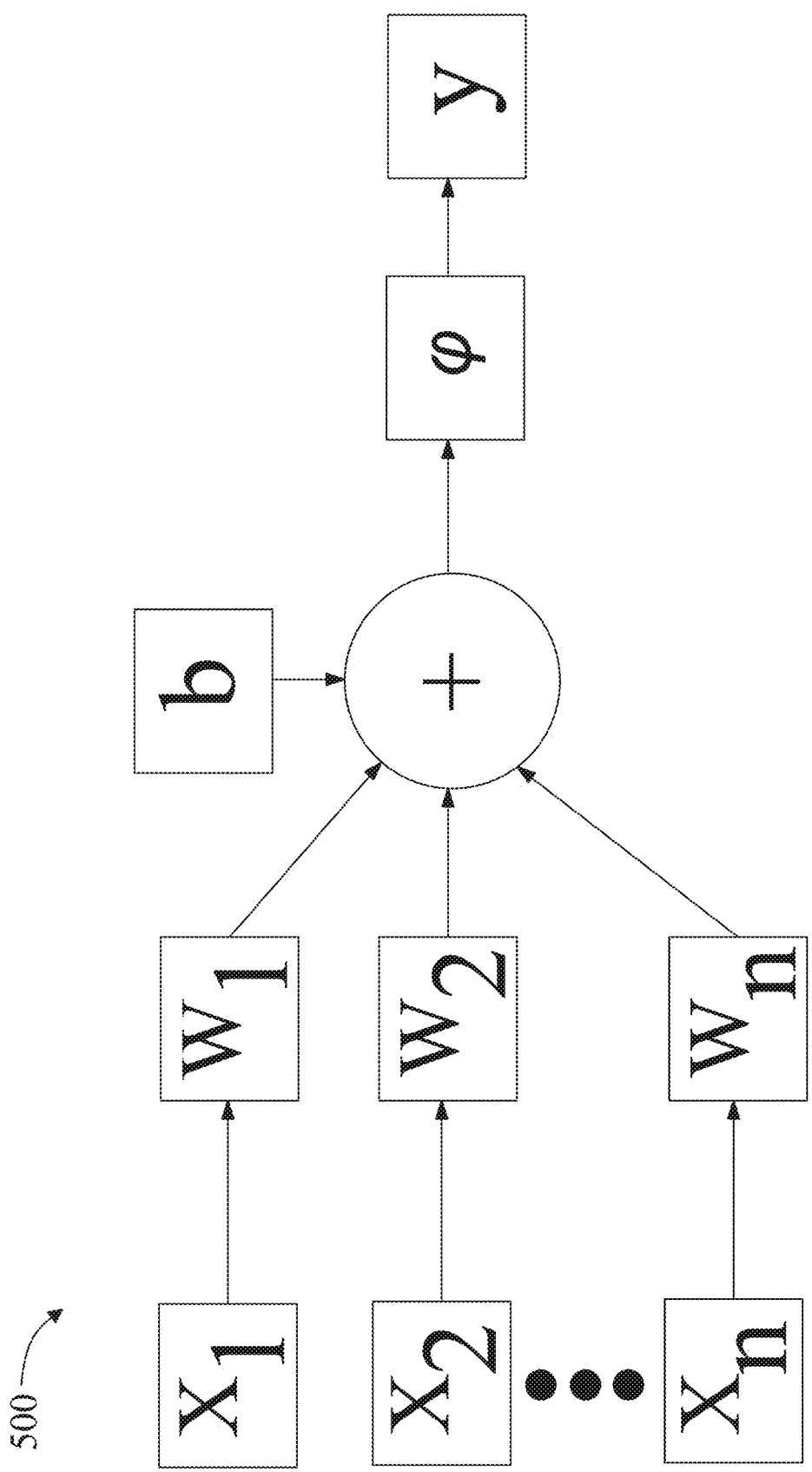
FIG. 5 is a diagram of an exemplary embodiment of a node of a neural network.

Referring now to FIG. 5, an exemplary embodiment of a node 500 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of a (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input $x_i$ may indicate whether the input is "excitatory," indicating that it has strong influence on the one or more outputs y, In a non-limiting embodiment by the corresponding weight having a large numerical value, and/or a "inhibitory," indicating it has a weak effect influence on the one more inputs y, In a non-limiting embodiment by the corresponding weight having a small numerical value. The values of weights $w_i$ may be determined by training a neural network using training data, which may be performed using any suitable process as described above.

Figure 6:
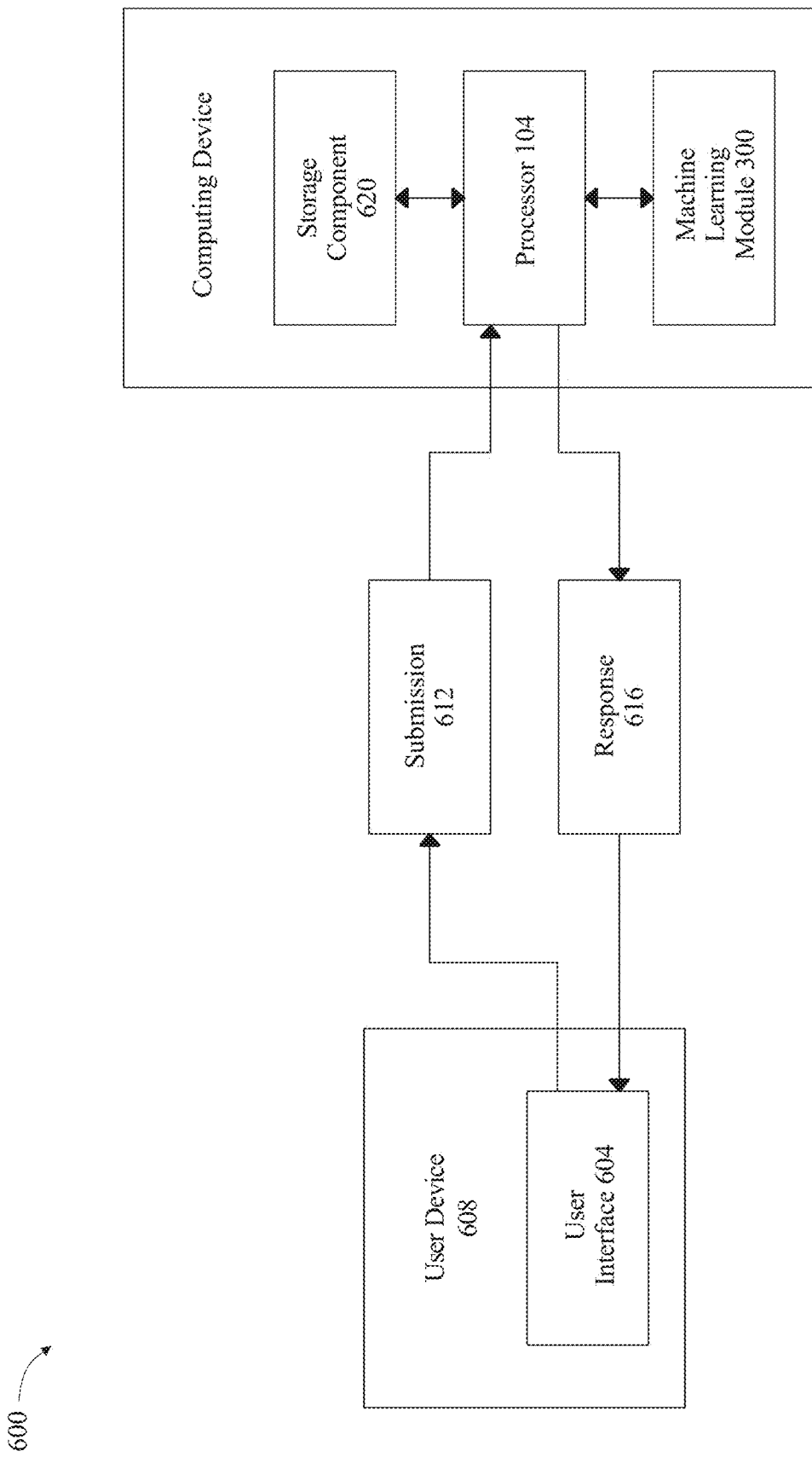
FIG. 6 is an exemplary embodiment of a chatbot system.

Referring now to FIG. 6, in one or more embodiments, system 100 may perform one or more of its functions, such as outputting execution sequence data, by implementing at least a chatbot system 600, an exemplary embodiment of which is schematically illustrated. In one or more embodiments, a user interface 604 may be communicatively connected with a computing device that is configured to operate a chatbot. In some cases, user interface 604 may be local to computing device. Alternatively, or additionally, in some other cases, user interface 604 may be remote to computing device, e.g., as part of a user device 608, and communicative with the computing device and processor 104 therein, by way of one or more networks, such as without limitation the internet. Alternatively, or additionally, user interface 604 may communicate with user interface 604 and/or computing device using telephonic devices and networks, such as without limitation fax machines, short message service (SMS), or multimedia message service (MMS). Commonly, user interface 604 may communicate with computing device using text-based communication, for example without limitation using a character encoding protocol, such as American Standard for Information Interchange (ASCII). Typically, user interface 604 may conversationally interface a chatbot, by way of at least a submission 612, from the user interface 604 to the chatbot, and a response 616, from the chatbot to the user interface 604. In many cases, one, or both, of submission 612 and response 616 are text-based communication. Alternatively, or additionally, in some cases, one or both of submission 612 and response 616 are audio-based communication.

With continued reference to FIG. 6, submission 612, once received by user interface 604 and/or computing device that operates a chatbot, may be processed by processor 104. In one or more embodiments, processor 104 may process submission 612 using one or more of keyword recognition, pattern matching, and natural language processing. In one or more embodiments, processor 104 may employ real-time learning with evolutionary algorithms. In one or more embodiments, processor 104 may retrieve a pre-prepared response from at least a storage component 620, based upon submission 612. Alternatively, or additionally, in one or more embodiments, processor 104 may communicate a response 616 without first receiving a submission 612, thereby initiating a conversation. In some cases, processor 104 may communicate an inquiry to user interface 604 and/or computing device, wherein processor 104 is configured to process an answer to the inquiry in a following submission 612 from the user interface 604 and/or computing device. In some cases, an answer to an inquiry presented within submission 612 from user interface 604 and/or computing device may be used by the computing device as an input to another function.

Figure 7:
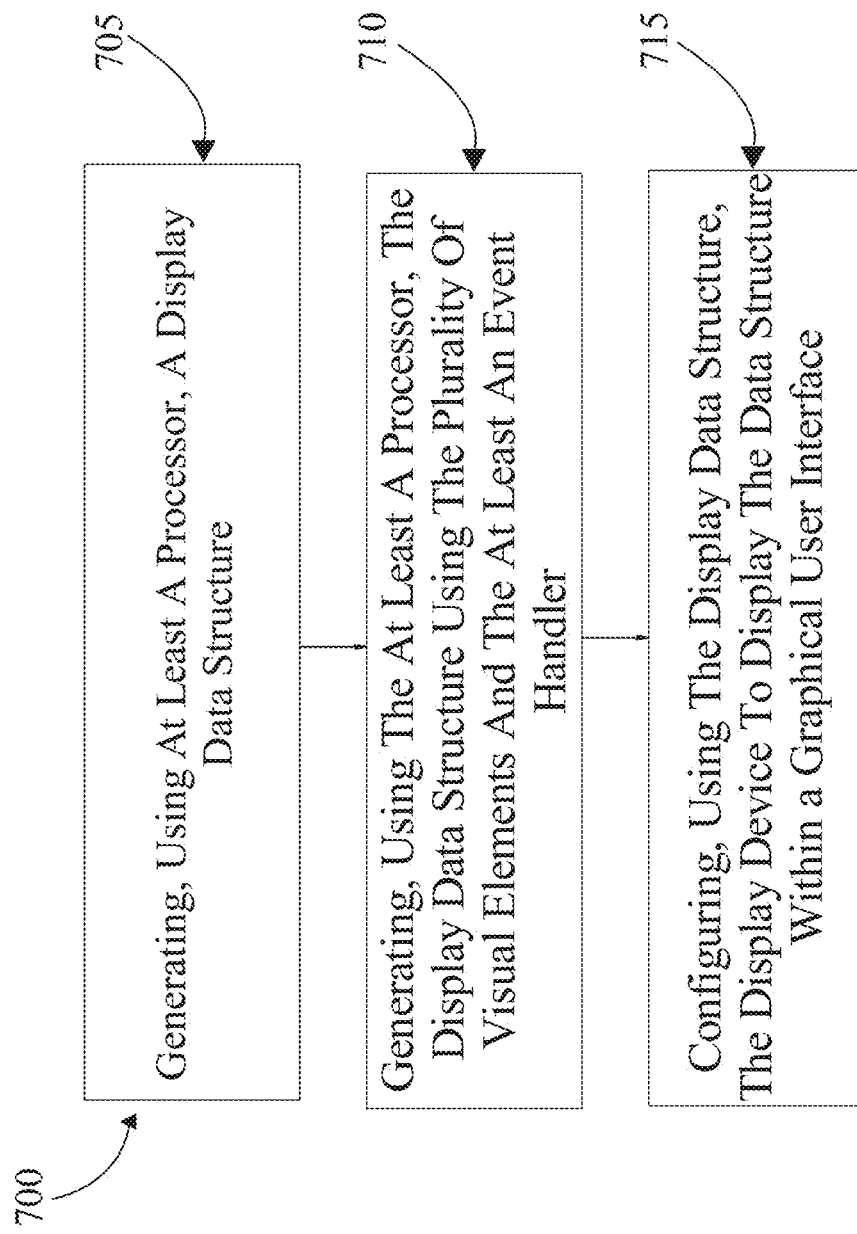
FIG. 7 is a block diagram of an exemplary embodiment of a method for generating a visual representation of a execution sequence within a graphical user interface.

Referring now to FIG. 7, a method for generating a visual representation of an execution sequence is illustrated. At step 705, method 700 includes generating, by at least a processor, a display data structure. In an embodiment, generating the display data structure includes providing a plurality of visual elements associated with execution sequence data and action sequence data and at least an event handler; linking a first visual element to the execution sequence data, wherein the execution sequence data includes specific execution sequence data; linking a second visual element to the action sequence data; verifying the action sequence data using a verification module; adjust the execution sequence data as a function of the verified action sequence data; classify the adjusted execution sequence data to a status using a classifier; linking a third visual element to the status. This may be implemented with reference to FIGS. 1-6.

Still referring to FIG. 7, at step 710, method 700 includes generating, by the at least a processor, the display data structure using the plurality of visual elements and the at least an event handler. This may be implemented with reference to FIGS. 1-6.

Still referring to FIG. 7, at step 715, method 700 includes configuring, using the display data structure, the display device to display the display data structure. This may be implemented with reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
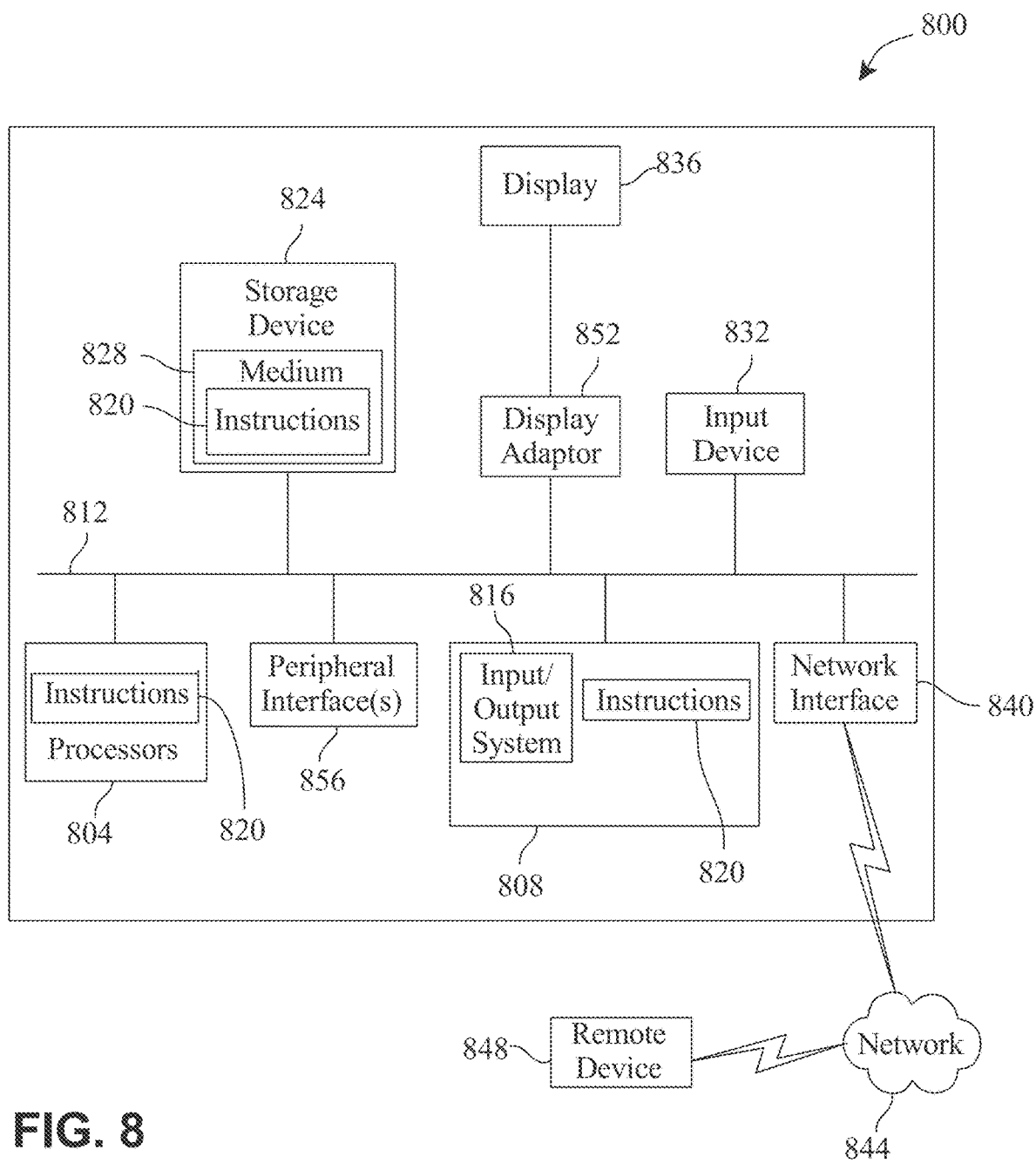
FIG. 8 is a block diagram of a computing system that can be used to implement any one or more of the methodologies disclosed herein and any one or more portions thereof. The drawings are not necessarily to scale and may be illustrated by phantom lines, diagrammatic representations and fragmentary views. In certain instances, details that are not necessary for an understanding of the embodiments or that render other details difficult to perceive may have been omitted.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display 836. Examples of a display device include, but are not limited to, a liquid crystal display (LCD), a cathode ray tube (CRT), a plasma display, a light emitting diode (LED) display, and any combinations thereof. Display adapter 852 and display 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a visual representation of an execution sequence within a graphical user interface, wherein the system comprises: a display device, wherein the display device is configured to display a graphical user interface (GUI); at least a computing device, wherein the computing device comprises: a memory; and at least a processor communicatively connected to the memory, wherein the memory contains instructions configuring the at least a processor to: generate a display data structure, wherein generating the display data structure further comprises: providing a plurality of visual elements and at least an event handler; linking a first visual element to execution sequence data, wherein the execution sequence data comprises specific execution sequence data; linking a second visual element to action sequence data; verifying the action sequence data using a verification module; generate adjusted execution sequence data as a function of the verified action sequence data; classify the adjusted execution sequence data to a status using a classifier; linking a third visual element to the status; generate the display data structure using the plurality of visual elements and the at least an event handler; and configure, using the display data structure, the display device to display the display data structure within a graphical user interface,
    wherein the at least a processor is further configured to: calculate a predicted execution sequence interval for the specific execution sequence data as a function of cluster execution sequence data and real-time execution sequence; and display, using the graphical user interface, a predicted execution sequence completion time as a function of the predicted execution sequence interval.

2. The system of claim 1, wherein linking the third visual element to the status comprises modifying a visual parameter associated with the status.

3. The system of claim 1, wherein the graphic user interface is configured to display at least a command corresponding to the plurality of visual elements.

4. The system of claim 1, wherein the graphical user interface is modified using an interface simulator, wherein the interface simulator is configured to adjust a visual element of the plurality of visual elements as a function of a comparison between the execution sequence data and the action sequence data.

5. The system of claim 4, wherein the interface simulator is generated using a machine learning model trained using training data configured to correlate cluster execution sequence data to example action sequence data.

6. The system of claim 1, wherein the at least a processor is further configured to assign a priority ranking to the predicted execution sequence interval.

7. The system of claim 1, wherein generating the display data structure comprises generating real-time alerts as a function of a threshold associated with the status.

8. The system of claim 1, wherein the graphical user interface comprises a filter option configured to sort the specific execution sequence data as a function of the status.

9. The system of claim 1, wherein the graphical user interface comprises a drag-and-drop functionality configured to: perform at least an adjustment to the status; and update the third visual element as a function of the at least an adjustment to the status.

10. A method for generating a visual representation of a execution sequence within a graphical user interface, wherein the method comprises: generating, using at least a processor, a display data structure, wherein generating the display data structure further comprises: providing a plurality of visual elements and at least an event handler; linking a first visual element to execution sequence data, wherein the execution sequence data comprises specific execution sequence data; linking a second visual element to action sequence data; verifying the action sequence data using a verification module; generate adjusted execution sequence data as a function of the verified action sequence data; classify the adjusted execution sequence data to a status using a classifier; linking a third visual element to the status; generating, using the at least a processor, the display data structure using the plurality of visual elements and the at least an event handler; and configuring, using the display data structure, a display device to display the display data structure within a graphical user interface,
wherein the at least a processor is further configured to:
calculate a predicted execution sequence interval for the specific execution sequence data as a function of cluster execution sequence data and real-time execution sequence; and display, using the graphical user interface, a predicted execution sequence completion time as a function of the predicted execution sequence interval.

11. The method of claim 10, wherein linking the third visual element to the status comprises modifying a visual parameter associated with the status.

12. The method of claim 10, wherein the graphical user interface is configured to display at least a command corresponding to the plurality of visual elements.

13. The method of claim 10, wherein the graphical user interface is modified using an interface simulator, wherein the interface simulator is configured to adjust the a visual element of the plurality of visual elements as a function of a comparison between the execution sequence data and the action sequence data.

14. The method of claim 13, wherein the interface simulator is generated using a machine learning model trained using training data configured to correlate cluster execution sequence data to example action sequence data.

15. The method of claim 10, wherein the at least a processor is further configured to assign a priority ranking to the predicted execution sequence interval.

16. The method of claim 10, wherein generating the display data structure comprises generating real-time alerts as a function of a threshold associated with the status.

17. The method of claim 10, wherein the graphical user interface comprises a filter option configured to sort the specific execution sequence data as a function of the status.

18. The method of claim 10, wherein the graphical user interface comprises a drag-and-drop functionality configured to: perform at least an adjustment to the status; and update the third visual element as a function of the at least an adjustment to the status.

* * * * *